US012692303B1

(12) United States Patent
Qiu et al.

(10) Patent No.: US 12,692,303 B1
(45) Date of Patent: Jul. 28, 2026

(54) ANTI-HUMAN INTERLEUKIN 23 MONOCLONAL ANTIBODY AND APPLICATION THEREOF

(71) Applicant: QYUNS THERAPEUTICS CO., LTD., Jiangsu (CN)

(72) Inventors: Jiwan Qiu, Jiangsu (CN); Yong Kong, Jiangsu (CN); Wei Chen, Jiangsu (CN); Huaiyao Qiao, Jiangsu (CN); Zhihua Qiu, Jiangsu (CN); Yiliang Wu, Jiangsu (CN); Tao Chen, Jiangsu (CN); Meijuan Wu, Jiangsu (CN)

(73) Assignee: QYUNS THERAPEUTICS CO., LTD., Jiangsu (CN)

( * ) Notice: Subject to any disclaimer, the term of this patent is extended or adjusted under 35 U.S.C. 154(b) by 624 days.

(21) Appl. No.: 18/009,849

(22) PCT Filed: Sep. 9, 2020

(86) PCT No.: PCT/CN2020/114176
§ 371 (c)(1),
(2) Date: Dec. 12, 2022

(87) PCT Pub. No.: WO2021/248718
PCT Pub. Date: Dec. 16, 2021

(30) Foreign Application Priority Data

Jun. 12, 2020 (CN) ........................ 202010534153.X

(51) Int. Cl.
*C07K 16/24* (2006.01)
*A61P 17/06* (2006.01)
(52) U.S. Cl.
CPC ............ *C07K 16/244* (2013.01); *A61P 17/06* (2018.01); *C07K 2317/24* (2013.01); *C07K 2317/565* (2013.01); *C07K 2317/76* (2013.01); *C07K 2317/92* (2013.01)
(58) Field of Classification Search
None
See application file for complete search history.

(56) References Cited

U.S. PATENT DOCUMENTS

| | | | |
|---|---|---|---|
| 7,872,102 B2 | 1/2011 | Beidler et al. | |
| 2007/0009526 A1 | 1/2007 | Benson et al. | |
| 2013/0315911 A1 | 11/2013 | Stevens et al. | |
| 2020/0138943 A1 | 5/2020 | Benson et al. | |

FOREIGN PATENT DOCUMENTS

| | | |
|---|---|---|
| CN | 101252951 | 8/2008 |
| CN | 101389351 | 3/2009 |
| CN | 105307681 | 2/2016 |
| CN | 108064249 | 5/2018 |
| CN | 110407936 | 11/2019 |
| CN | 111718414 | 3/2021 |
| EP | 3 904 382 | 11/2021 |
| EP | 4166568 | 4/2023 |
| WO | 2007/005955 | 1/2007 |
| WO | 2007/076524 | 7/2007 |
| WO | 2008/103432 | 8/2008 |
| WO | 2008/103473 | 8/2008 |
| WO | 2011/056600 | 5/2011 |
| WO | 2013/165791 | 11/2013 |
| WO | 2014/137962 | 9/2014 |
| WO | 2016/073406 | 5/2016 |
| WO | 2020/108530 | 6/2020 |

OTHER PUBLICATIONS

PR Newswire. Seneca Biopharma and QYuns Therapeutics sign term sheet for global licensing of novel monoclonal antibodies for treating auto-immune diseases. (Oct. 2019) (Year: 2019).*
Li et al. Safety and Efficacy of Anti-IL-23 Monoclonal Antibody QX004N for Patients With Psoriasis A Randomized Clinical Trial. JAMA Dermatol.2025;161(3):247-255. (Year: 2025).*
Extended European Search Report issued Nov. 7, 2023 in European Patent Application No. 20940419.3.
International Search Report issued Mar. 16, 2021, in International (PCT) Application No. PCT/CN2020/114176, with English translation.

* cited by examiner

*Primary Examiner* — Maher M Haddad
(74) *Attorney, Agent, or Firm* — Wenderoth, Lind & Ponack, L.L.P.

(57) ABSTRACT

The present invention relates to an anti-human interleukin 23 (hIL-23) monoclonal antibody and an application thereof. The anti-human interleukin 23 (hIL-23) monoclonal antibody comprises three heavy chain complementary determining regions (CDR-H1, CDR-H2 and CDR-H3) and three light chain complementary determining regions (CDR-L1, CDR-L2 and CDR-L3), wherein (a): the amino acid sequence of the CDR-H1 is as shown in SEQ ID NO: 1, (b): the amino acid sequence of the CDR-H2 is as shown in SEQ ID NO: 2, (c): the amino acid sequence of the CDR-H3 is as shown in SEQ ID NO: 3, (d): the amino acid sequence of the CDR-L1 is as shown in SEQ ID NO: 4, (e): the amino acid sequence of the CDR-L2 is as shown in SEQ ID NO: 5, and (f): the amino acid sequence of the CDR-L3 is as shown in SEQ ID NO: 6. Compared with existing anti-human interleukin 23 monoclonal antibodies (Guselkumab and Risankizumab), the hIL-23 binding affinity of the anti-human interleukin 23 (hIL-23) monoclonal antibody is equivalent, but the antagonistic activity at the cellular level is superior to Guselkumab, and equivalent to Risankizumab.

5 Claims, 4 Drawing Sheets

Specification includes a Sequence Listing.

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence

<400> SEQUENCE: 1

Asn His Glu Met Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic sequence

<400> SEQUENCE: 2

Ile Ile Thr Thr Ser Asp Thr Thr Tyr Tyr Ala Thr Trp Ala Lys Gly
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic sequence

<400> SEQUENCE: 3

Val Asp Ile Val Leu Leu Ser Val Thr Ser Arg Ile
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence

<400> SEQUENCE: 4

Gln Ala Ser Gln Ser Val Ser Thr Tyr Leu Ser
1               5                   10

<210> SEQ ID NO 5
<211> LENGTH: 7
```

<212> TYPE: PRT
<213> ORGANISM: Artificial Sequence
<220> FEATURE:
<223> OTHER INFORMATION: Synthetic sequence

<400> SEQUENCE: 5

Gly Ala Ser Asn Leu Glu Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic sequence

<400> SEQUENCE: 6

Gln Ser Gly Tyr Val Phe Ala Gly Leu Thr
1               5                   10

<210> SEQ ID NO 7
<211> LENGTH: 120
<212> TYPE: PRT
<213> ORGANISM: Artificial Sequence
<220> FEATURE:
<223> OTHER INFORMATION: Synthetic sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn His
            20                  25                  30

Glu Met Ser Trp Val Arg Gln Ala Pro Gly Lys Gly Leu Glu Trp Ile
        35                  40                  45

Gly Ile Ile Thr Thr Ser Asp Thr Thr Tyr Tyr Ala Thr Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Val Asp Ile Val Leu Leu Ser Val Thr Ser Arg Ile Trp Gly Gln
            100                 105                 110

Gly Thr Leu Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Synthetic sequence

<400> SEQUENCE: 8

Asp Val Val Met Thr Gln Ser Pro Ser Ser Leu Ser Ala Ser Val Gly
1               5                   10                  15

Asp Arg Val Thr Ile Thr Cys Gln Ala Ser Gln Ser Val Ser Thr Tyr
            20                  25                  30

Leu Ser Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Gly Tyr Val Phe Ala Gly
                85                  90                  95

Leu Thr Phe Gly Gly Gly Thr Lys Val Glu Ile Lys
            100                 105

<210> SEQ ID NO 9
<211> LENGTH: 189
<212> TYPE: PRT
<213> ORGANISM: Artificial Sequence
<220> FEATURE:
<223> OTHER INFORMATION: Synthetic sequence

<400> SEQUENCE: 9

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr
        50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 10
<211> LENGTH: 328
<212> TYPE: PRT
<213> ORGANISM: Artificial Sequence
<220> FEATURE:
<223> OTHER INFORMATION: Synthetic sequence

<400> SEQUENCE: 10

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

-continued

```
Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

```
<210> SEQ ID NO 11
<211> LENGTH: 450
<212> TYPE: PRT
<213> ORGANISM: Artificial Sequence
<220> FEATURE:
<223> OTHER INFORMATION: Synthetic sequence

<400> SEQUENCE: 11
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn His
            20                  25                  30

Glu Met Ser Trp Val Arg Gln Ala Pro Gly Lys Gly Leu Glu Trp Ile
        35                  40                  45

Gly Ile Ile Thr Thr Ser Asp Thr Thr Tyr Tyr Ala Thr Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Asp Ile Val Leu Leu Ser Val Thr Ser Arg Ile Trp Gly Gln
            100                 105                 110
```

-continued

```
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450
```

```
<210> SEQ ID NO 12
<211> LENGTH: 215
<212> TYPE: PRT
<213> ORGANISM: Artificial Sequence
<220> FEATURE:
<223> OTHER INFORMATION: Synthetic sequence

<400> SEQUENCE: 12

Asp Val Val Met Thr Gln Ser Pro Ser Ser Leu Ser Ala Ser Val Gly
1               5                   10                  15
```

-continued

```
Asp Arg Val Thr Ile Thr Cys Gln Ala Ser Gln Ser Val Ser Thr Tyr
         20              25              30

Leu Ser Trp Tyr Gln Gln Lys Pro Gly Lys Ala Pro Lys Leu Leu Ile
         35              40              45

Tyr Gly Ala Ser Asn Leu Glu Ser Gly Val Pro Ser Arg Phe Ser Gly
     50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Ser Gly Tyr Val Phe Ala Gly
             85              90              95

Leu Thr Phe Gly Gly Gly Thr Lys Val Glu Ile Lys Arg Thr Val Ala
             100             105             110

Ala Pro Ser Val Phe Ile Phe Pro Pro Ser Asp Glu Gln Leu Lys Ser
         115             120             125

Gly Thr Ala Ser Val Val Cys Leu Leu Asn Asn Phe Tyr Pro Arg Glu
     130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
             165             170             175

Ser Ser Thr Leu Thr Leu Ser Lys Ala Asp Tyr Glu Lys His Lys Val
             180             185             190

Tyr Ala Cys Glu Val Thr His Gln Gly Leu Ser Ser Pro Val Thr Lys
         195             200             205

Ser Phe Asn Arg Gly Glu Cys
     210             215
```

ANTI-HUMAN INTERLEUKIN 23 MONOCLONAL ANTIBODY AND APPLICATION THEREOF

TECHNICAL FIELD

The present application relates to the field of antibody drugs. Particularly, the present application relates to a monoclonal antibody against human interleukin 23 (hIL-23) and a use thereof.

BACKGROUND ART

IL-23 is mainly produced by activated dendritic cells, macrophages and monocytes, etc. It is a member of the IL-12 heterodimer cytokine family, mainly composed of IL-23p19 and IL-12/IL-23p40 subunits. IL-23 receptors comprise 2 subunits which are IL-12 receptor β1 and IL-23 receptor. IL-23 activates downstream signal pathways to exert biological functions by expressing receptors IL-23R and IL-12R β1 on the surface of T cells, NK cells, and monocyte macrophages/dendritic cells. IL-23 mainly acts on Th17 cells and induces them to produce proinflammatory cytokines such as IL-17A, IL-17F, IL-21, IL-22, etc., and plays an important role in autoimmune and inflammatory diseases such as psoriasis, psoriatic arthritis, multiple sclerosis, Crohn's disease, inflammatory bowel disease, etc.

IL-23 mediated signal transduction and biological effects are related to many types of diseases, including rheumatoid arthritis, juvenile rheumatoid arthritis, systemic juvenile rheumatoid arthritis, psoriatic arthritis, ankylosing spondylitis, osteoarthritis, gastric ulcer, inflammatory bowel disease, ulcerative colitis, acute pancreatitis, primary biliary cirrhosis, Hashimoto's thyroiditis, systemic lupus erythematosus, iridocyclitis, uveitis, optic neuritis, idiopathic pulmonary fibrosis, systemic vasculitis/Wegener's granuloma, allergic/atopic disease, asthma, allergic rhinitis, eczema, adult respiratory distress syndrome, allergic contact dermatitis, vitiligo, psoriasis, alopecia areata, pemphigus, scleroderma, allergic/atopic conjunctivitis, allergic pneumonia, organ transplant rejection, graft versus host disease, systemic inflammatory response syndrome, Graves' disease, Raynaud's disease, type B insulin resistance diabetes, myasthenia gravis, nephrotic syndrome, nephritis, glomerulonephritis and/or acute renal failure, etc.

Guselkumab (trade name Tremfya) and Risankizumab (trade name SKYRIZI), monoclonal antibody drugs targeting IL-23 developed by Johnson & Johnson and Abbvie respectively, have been approved by the US FDA to treat psoriasis and psoriatic arthritis, and to carry out phase III clinical research on Crohn's disease and inflammatory bowel disease.

SUMMARY OF THE APPLICATION

The object of the present application is to provide a new anti-human interleukin-23 (hIL-23) monoclonal antibody, a pharmaceutical composition comprising the monoclonal antibody and pharmaceutical use of the monoclonal antibody.

That is, the present application comprises:

1. An isolated anti-human interleukin23 monoclonal antibody, comprising three heavy chain complementary determining regions (CDR-H1, CDR-H2 and CDR-H3) and three light chain complementary determining regions (CDR-L1, CDR-L2 and CDR-L3), wherein:

(a) the amino acid sequence of CDR-H1 (CDR-H1 represents heavy chain CDK1 in this specification) is represented by SEQ ID NO: 1 (NHEMS);

(b) the amino acid sequence of CDR-H2 (CDR-H2 represents heavy chain CDR2 in this specification) is represented by SEQ ID NO: 2 (IITTSDTTYYATWAKG);

(c) the amino acid sequence of CDR-H3 (CDR-H3 represents heavy chain CDR3 in this specification) is represented by SEQ ID NO: 3 (VDIVLLSVTSRI);

(d) the amino acid sequence of CDR-L1 (CDR-L1 represents light chain CDR1 in this specification) is represented by SEQ ID NO: 4 (QASQSVSTYLS);

(e) the amino acid sequence of CDR-L2 (CDR-L2 represents light chain CDR2 in this specification) is represented by SEQ ID NO: 5 (GASNLES); and (f) the amino acid sequence of CDR-L3 (CDR-L3 represents light chain CDR3 in this specification) is represented by SEQ ID NO: 6 (QSGYVFAGLT).

2. The monoclonal antibody according to item 1, which comprises a heavy chain variable region and a light chain variable region, wherein, the amino acid sequence of the heavy chain variable region is represented by SEQ ID NO: 7, and the amino acid sequence is

```
EVQLVESGGGLVQPGGSLRLSCAASGFSLSNHEMSWVRQAPGKGLEWIG

IITTSDTTYYATWAKGRFTISRDNSKNTLYLQMNSLRAEDTAVYYCARV

DIVLLSVTSRIWGQGTLVTVSS;
``` and, the amino acid sequence of the light chain variable region is represented by SEQ the amino acid sequence is ID NO: 8, and

```
DVVMTQSPSSLSASVGDRVTITCQASQSVSTYLSWYQQKPGKAPKLLIY

GASNLESGVPSRFSGSGSGTDFTLTISSLQPEDFATYYCQSGYVFAGLT

FGGGTKVEIK.
```

3. An isolated nucleic acid, encoding the monoclonal antibody of any one of the aforementioned items.

4. A host cell, comprising the nucleic acid according to item 3.

The nucleic acid can be present on a vector. The vector can be of any type, for example, a recombinant vector such as an expression vector. Any one of a variety of host cells can be used. In one embodiment, the host cell is a prokaryotic cell, for example, *Escherichia coli* (*E. coli*). In another embodiment, the host cell is a eukaryotic cell, for example, a mammalian cell such as a Chinese hamster ovary (CHO) cell.

5. A method for producing a monoclonal antibody, comprising culturing the host cell according to item 4 to produce the monoclonal antibody of any one of the aforementioned items.

The method includes expressing a recombinant vector encoding the anti-human interleukin 23 monoclonal antibody in a suitable host cell, thereby producing the monoclonal antibody. In certain embodiments, the method includes culturing a host cell comprising a nucleic acid encoding the anti-human interleukin 23 monoclonal antibody, thereby expressing the nucleic acid. The method may further include recovering the anti-human interleukin 23 monoclonal antibody from a host cell culture or host cell culture medium.

6. A pharmaceutical composition, comprising the monoclonal antibody of any one of the aforementioned items and a pharmaceutically acceptable carrier.

The pharmaceutical composition may further comprise an additional therapeutic agent (for example, a different anti-human interleukin23 (hIL-23) antibody).

7. The pharmaceutical composition according to item 6, which is used for treatment of a disease related to IL-23 mediated signal transduction.

8. The pharmaceutical composition according to item 7, wherein the disease related to IL-23 mediated signal transduction is selected from the group consisting of: rheumatoid arthritis, juvenile rheumatoid arthritis, systemic juvenile rheumatoid arthritis, psoriatic arthritis, ankylosing spondylitis, osteoarthritis, gastric ulcer, inflammatory bowel disease, ulcerative colitis, acute pancreatitis, primary biliary cirrhosis, Hashimoto's thyroiditis, systemic lupus erythematosus, iridocyclitis, uveitis, optic neuritis, idiopathic pulmonary fibrosis, systemic vasculitis/Wegener's granuloma, allergic/atopic disease, asthma, allergic rhinitis, eczema, adult respiratory distress syndrome, allergic contact dermatitis, vitiligo, psoriasis, alopecia areata, pemphigus, scleroderma, allergic conjunctivitis, allergic pneumonia, organ transplant rejection, graft versus host disease, systemic inflammatory response syndrome, Graves' disease, Raynaud's disease, type B insulin resistance diabetes, myasthenia gravis, nephrotic syndrome, nephritis, glomerulonephritis and/or acute renal failure.

9. Use of the monoclonal antibody of any one of the aforementioned items in the preparation of a medicament for treatment of a disease related to IL-23 mediated signal transduction.

10. The use according to item 9, wherein the disease related to IL-23 mediated signal transduction is selected from the group consisting of: rheumatoid arthritis, juvenile rheumatoid arthritis, systemic juvenile rheumatoid arthritis, psoriatic arthritis, ankylosing spondylitis, osteoarthritis, gastric ulcer, inflammatory bowel disease, ulcerative colitis, acute pancreatitis, primary biliary cirrhosis, Hashimoto's thyroiditis, systemic lupus erythematosus, iridocyclitis, uveitis, optic neuritis, idiopathic pulmonary fibrosis, systemic vasculitis/Wegener's granuloma, allergic/atopic disease, asthma, allergic rhinitis, eczema, adult respiratory distress syndrome, allergic contact dermatitis, vitiligo, psoriasis, alopecia areata, pemphigus, scleroderma, allergic conjunctivitis, allergic pneumonia, organ transplant rejection, graft versus host disease, systemic inflammatory response syndrome, Graves' disease, Raynaud's disease, type B insulin resistance diabetes, myasthenia gravis, nephrotic syndrome, nephritis, glomerulonephritis and/or acute renal failure.

11. A method for treating a disease related to IL-23 mediated signal transduction, including:

administering the monoclonal antibody according to any one of the aforementioned items or the pharmaceutical composition according to any one of the aforementioned items to a subject in need thereof.

12. The method according to item 11, wherein the disease related to IL-23 mediated signal transduction is selected from the group consisting of: rheumatoid arthritis, juvenile rheumatoid arthritis, systemic juvenile rheumatoid arthritis, psoriatic arthritis, ankylosing spondylitis, osteoarthritis, gastric ulcer, inflammatory bowel disease, ulcerative colitis, acute pancreatitis, primary biliary cirrhosis, Hashimoto's thyroiditis, systemic lupus erythematosus, iridocyclitis, uveitis, optic neuritis, idiopathic pulmonary fibrosis, systemic vasculitis/Wegener's granuloma, allergic/atopic disease, asthma, allergic rhinitis, eczema, adult respiratory distress syndrome, allergic contact dermatitis, vitiligo, psoriasis, alopecia areata, pemphigus, scleroderma, allergic conjunctivitis, allergic pneumonia, organ transplant rejection, graft versus host disease, systemic inflammatory response syndrome, Graves' disease, Raynaud's disease, type B insulin resistance diabetes, myasthenia gravis, nephrotic syndrome, nephritis, glomerulonephritis and/or acute renal failure.

13. The method according to item 12, wherein the systemic vasculitis is Wegener's granuloma.

Effect of the Application

The present application provides a new anti-human interleukin 23 (hIL-23) monoclonal antibody. Compared with the existing anti-human interleukin 23 monoclonal antibodies (Guselkumab and Risankizumab), it has a comparable affinity for binding to hIL-23, but its antagonistic activity at the cellular level is superior to that of Guselkumab, and is comparable to that of Risankizumab.

It should be noted that Risankizumab (SKYRIZIR) has been approved for marketing in Japan, the United States and the European Union, and the clinical trial results show that its therapeutic effect on moderate to severe plaque psoriasis is superior to that of Johnson & Johnson's blockbuster anti-inflammatory drug STELARA® (ustekinumab) and AbbVie's best-selling anti-inflammatory drug HUMIRA® (adalimumab).

The monoclonal antibody of the present application shows antagonistic activity comparable to Risankizumab at the cell level, and it is expected to show good clinical effects in the prevention and treatment of related diseases.

SPECIFIC EMBODIMENTS

Figure 1:
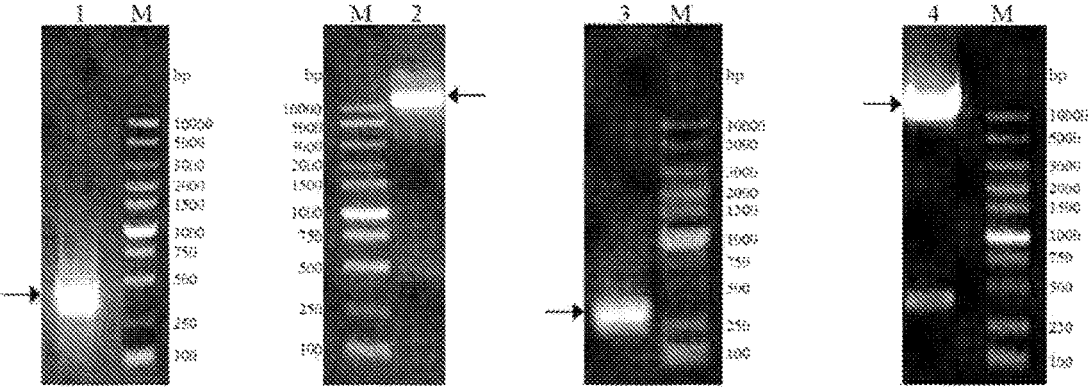
FIG. 1 shows the results of nucleic acid electrophoresis of the constructed QX004N (HZD90-32) transient expression plasmid, wherein, M: Marker; Band 1: PCR product 90VH-Hu18; Band 2: pHZDCH, HindIII/NheI; Band 3: PCR product 90VK-Hu9; Band 4: pHZDCK, HindIII/BsiWI.

The scientific and technological terms mentioned in this specification have the same meanings as those commonly understood by those skilled in the art. In case of any conflict, the definitions in this specification shall prevail.

In general, the terms used in this specification have the following meanings.

In this specification, "isolated" antibody is an antibody that has been separated from a component of its natural environment. In certain embodiments, the antibody is purified to a purity greater than 95% or 99%, which is determined by, for example, electrophoresis (for example, SDS-PAGE isoelectric focusing (IEF), capillary electrophoresis) or chromatography (for example, ion exchange or reverse phase HPLC). For a review of methods for evaluating antibody purity, see, for example, Flatman et al., J. Chromatogr. B848:79-87 (2007).

In this specification, "monoclonal antibody" means an antibody derived from a population of substantially homologous antibodies, that is, each antibody constituting the population is the same and/or binds to the same epitope, except for possible variant antibodies (for example, comprising naturally occurring mutations or produced in the production process of monoclonal antibody products), such variants are usually present in trace amounts. Unlike polyclonal antibody products that generally comprise different antibodies directed against different determinants (epitopes), each monoclonal antibody of the monoclonal antibody product is directed against a single determinant on the antigen. Thus, the modifier "monoclonal" indicates the characteristic that the antibody is derived from a substantially homologous antibody population, and should not be interpreted as requiring the production of the antibody by any specific method. For example, the monoclonal antibody to be used according to the present application can be prepared by a variety of technologies; the technologies include, but are not limited to, a hybridoma method, a recombinant DNA method, a phage display method, and a method using a transgenic animal comprising all or part of the human immunoglobulin locus. Such methods and other exemplary methods for preparing monoclonal antibodies are described herein.

In this specification, "affinity" means the strength of the sum of non-covalent interactions between a single binding site of a molecule (for example, an antibody) and its binding partner (for example, an antigen). Unless otherwise noted, the "binding affinity" used in this specification means the inherent binding affinity reflecting the 1:1 interaction between members of a binding pair (for example, antibody and antigen). The affinity of molecule X to its partner Y can usually be denoted by the equilibrium dissociation constant ($K_D$). Affinity can be measured by common methods known in the art.

In this specification, human interleukin 23 (hIL-23) represents a human derived protein, which is a heterodimer consisting of p19 and p40 subunits. The amino acid sequence of p19 is represented by SEQ ID NO: 9, and the amino acid sequence of p40 is represented by SEQ ID NO: 10, wherein the underlined part represents a signal peptide.

SEQ ID NO: 9:
MLGSRAVMLLLLLPWTAQGRAVPGGSSPAWTQCQQLSQKLCTLAWSAHP

LVGHMDLREEGDEETTNDVPHIQCGDGCDPQGLRDNSQFCLQRIHQGLI

FYEKLLGSDIFTGEPSLLPDSPVGQLHASLLGLSQLLQPEGHHWETQQI

PSLSPSQPWQRLLLRFKILRSLQAFVAVAARVFAHGAATLSP

SEQ ID NO: 10:
MCHQQLVISWFSLVFLASPLVAIWELKKDVYVVELDWYPDAPGEMVVLT

CDTPEEDGITWTLDQSSEVLGSGKTLTIQVKEFGDAGQYTCHKGGEVLS

-continued

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCS

In this specification, "anti-human interleukin 23 monoclonal antibody" means a monoclonal antibody that can bind to human interleukin 23 with sufficient affinity, so that the monoclonal antibody can be used as a diagnostic agent and/or therapeutic agent targeting human interleukin 23.

The anti-human interleukin 23 (IL-23) monoclonal antibody in the present application does not bind to a target unrelated protein. Herein, "unrelated protein" refers to a protein except for the target human interleukin 23; Herein, "non-binding" means that when the binding ability of the anti-human interleukin-23 (IL-23) monoclonal antibody of the present application to its target human interleukin-23 is 100%, the binding ability of the anti-human interleukin-23 (IL-23) monoclonal antibody of the present application to the unrelated proteins is less than 10%, such as 9%, 8%, 7%, 6%, 5%, 4%, 3%, 2%, 1% or 0.

The anti-human interleukin 23 (IL-23) monoclonal antibody of the present application may not bind to interleukin 23 of other animal species. Herein, "other animal species" refers to other animal species except for human beings, such as rhesus monkey, cynomolgus monkey, rat, mouse, etc.; Herein, "non-binding" means that when the binding ability of the anti-human interleukin-23 (IL-23) monoclonal antibody of the present application to its target human interleukin-23 is 100%, the binding ability of the anti-human interleukin-23 (IL-23) monoclonal antibody of the present application to interleukin-23 of other animal species is less than 10%, such as 9%, 8%, 7%, 6%, 5%, 4%, 3%, 2%, 1% or 0.

The anti-human interleukin-23 (IL-23) monoclonal antibody of the present application has an equilibrium dissociation constant ($K_D$) of ≤1 µM, ≤100 nM, ≤50 nM or ≤40 nM.

The experimental results show that the anti-human interleukin-23 (IL-23) monoclonal antibody of the present application can specifically bind to the p19 subunit of human interleukin-23 (IL-23).

The anti-human interleukin 23 (IL-23) monoclonal antibody of the present application is comparable to or superior to the marketed similar monoclonal antibody products in many biological activities. The biological activity, such as activity of inhibiting phosphorylation of STAT3 in cells induced by IL-23, activity of inhibiting the release of IL-17A from mouse spleen cells induced by IL-23, and activity of inhibiting the release of IFN-γ from human NK cells induced by IL-23.

In one embodiment, the amino acid sequence of the heavy chain of the anti-human interleukin-23 (IL-23) monoclonal antibody of the present application is represented by SEQ ID NO: 11; the amino acid sequence of the light chain is represented by SEQ ID NO: 12.

SEQ ID NO: 11
EVQLVESGGGLVQPGGSLRLSCAASGFSLSNHEMSWVRQAPGKGLEWIG

IITTSDTTYYATWAKGRFTISRDNSKNTLYLQMNSLRAEDTAVYYCARV

7

-continued

DIVLLSVTSRIWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK

SEQ ID NO: 12
DVVMTQSPSSLSASVGDRVTITCQASQSVSTYLSWYQQKPGKAPKLLIY

GASNLESGVPSRFSGSGSGTDFTLTISSLQPEDFATYYCQSGYVFAGLT

FGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

Particularly, both of SEQ ID NO: 11 and SEQ ID NO: 12 are humanized sequences.

In this specification, "isolated" nucleic acid means a nucleic acid molecule that has been separated from a component of its natural environment. An isolated nucleic acid comprises a nucleic acid molecule contained in a cell that usually contains a nucleic acid molecule, but the nucleic acid molecule is present outside the chromosome or in a chromosome position different from its natural chromosome position.

In this specification, "isolated nucleic acid encoding anti-human interleukin 23 monoclonal antibody" means one or more nucleic acid molecules encoding heavy chains and light chains of the antibody, including such nucleic acid molecules in a single vector or separated vectors, and such nucleic acid molecules present in one or more positions in host cell.

In this specification, "vector" means a nucleic acid molecule capable of amplifying another nucleic acid linked to it. The term includes a vector as a self-replicating nucleic acid structure and a vector integrated into the genome of a host cell into which it has been introduced. Certain vectors can guide the expression of nucleic acids operatively linked to them. Such vectors are referred to herein as "expression vectors".

In this specification, "host cell", "host cell line" and "host cell culture" are used interchangeably, and refer to cells into which exogenous nucleic acid has been introduced, including the progeny of such cells. Host cells include "transformants" and "transformed cells", which include primary transformed cells and progeny derived therefrom (regardless of the number of passages). The progeny may not be identical with the parent cell in terms of nucleic acid content, but may comprise a mutation. The mutant progeny with the same function or biological activity screened or selected for initially transformed cells are included in this specification.

In this specification, "pharmaceutical composition" means a product that presents in a form that enables the biological activity of the active ingredient contained therein to take effects, and the composition does not contain additional components with unacceptable toxicity to the subject to which the preparation is to be administered.

In this specification, "pharmaceutically acceptable carrier" means an ingredient other than the active ingredient in the pharmaceutical composition, which is non-toxic to the subject. Pharmaceutically acceptable carriers include, but are not limited to, buffers, excipients, stabilizers or preservatives.

EXAMPLES

Hereinafter, the present application will be described in more detail through examples. It should be understood that the present application is not limited to these examples.

Example 1: Preparation of Anti-Human Interleukin 23 Monoclonal Antibody QX004N

Human interleukin 23 (IL-23) was purchased from Shanghai Novo protein Technology Co., Ltd. to immunize New Zealand rabbits. Antigen binding specific antibody clones were obtained through B cell cloning technology, and then monoclonal antibodies binding to IL-23 and having inhibitory activity against IL-23 were screened out. Firstly, the cell supernatant was detected by Binding ELISA, and clones binding to IL-23 were selected; then clones having inhibitory activity against IL-23 were selected by using Blocking ELISA detection. The above immunization and screening processes were entrusted to commercial companies.

Five clones were selected for recombinant expression and sequencing. The clone 90 # was humanized. NCBI IgBlast was used to perform homology comparison of human IgG germline sequences, IGHV3-66*01 was selected as the template for heavy chain CDR grafting, and the heavy chain CDR regions of the clone 90 #(i.e., CDR-H1 (SEQ ID No: 1), CDR-H2 (SEQ ID No: 2) and CDR-H3 (SEQ ID No: 3)) were grafted into the framework region of IGHV3-66*01; IGKV1-39*01 was selected as template for the light chain CDR grafting, and the light chain CDR regions of the clone 90 #(i.e. CDR-L1 (SEQ ID No: 4), CDR-L2 (SEQ ID No: 5) and CDR-L3 (SEQ ID No: 6)) were grafted into the framework region of IGKV1-39*01; Reverse mutation was carried out at the specific site of the framework region, and the methionine (Met, M) at position 103 in heavy chain CDR-H3 was mutated to leucine (Leu, L), to obtain the variable region of the monoclonal antibody QX004N of the present application. Finally, the amino acid sequence of the humanized heavy chain variable region is represented by SEQ ID NO: 7: the amino acid sequence of the humanized light chain variable region is represented by SEQ ID NO: 8.

The gene of the above heavy chain variable region (SEQ ID NO: 7) was obtained by PCR amplification: the gene of the light chain variable region (SEQ ID NO: 8) was obtained by PCR amplification. The heavy chain expression plasmid pHZDCH was digested with HindIII and NheI; the light chain expression plasmid pHZDCK was digested with HindIII and BsiWI; the PCR amplified genes were inserted into the corresponding expression plasmids with Infusion recombinant enzyme to construct the heavy chain expression plasmid pHZDCH-90VH-Hu18 and the light chain expression plasmid pHZDCK-90VK-Hu9.

The results of the double digestion of plasmids detected by nucleic acid electrophoresis are shown in FIG. 1. According to the results in FIG. 1, it can be seen the PCR amplification results of the heavy chain variable region and light chain variable region of the antibody and the results of double digestion of the heavy chain and light chain expression plasmids, wherein, the size of the plasmids of the heavy chains and light chains is about 10000 bp, the light chain variable region is about 438 bp, and the heavy chain variable region is about 459 bp.

Figure 2:
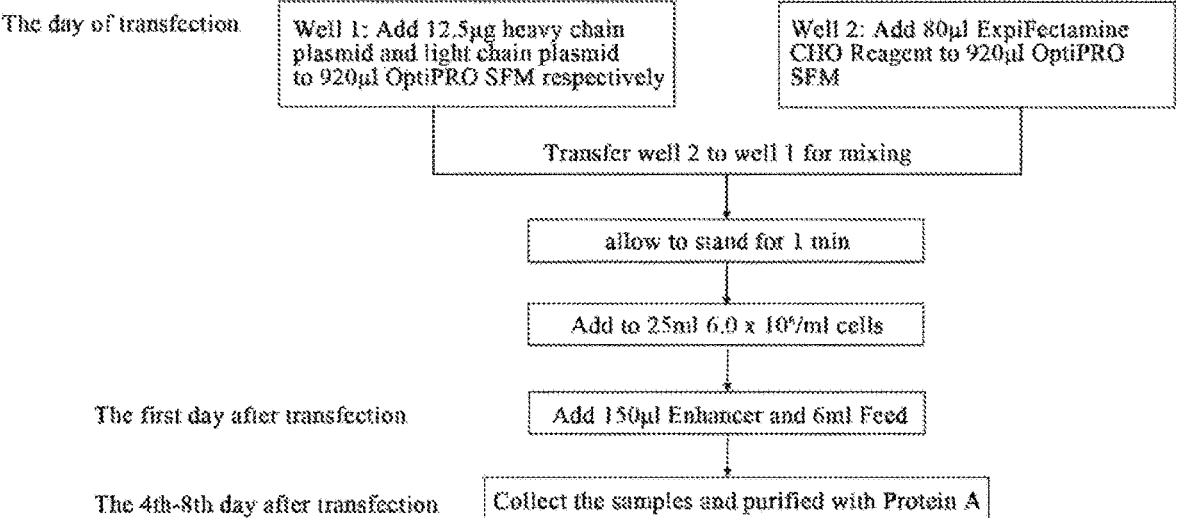
FIG. 2 is a flow chart of transient expression.

The heavy chain expression plasmid and light chain expression plasmid with correct sequence were co-transfected into ExpiCHO-S cells. The day before transfection, ExpiCHO-S cells were diluted to $3 \times 10^6$ cells/ml for passage before transfection. On the day of transfection, the cell density was diluted to $6 \times 10^6$ cells/ml, and 25 ml cells were placed in 125 ml shake flask, waiting for transfection. The process of transfection and expression is shown in FIG. 2.

Figure 3:
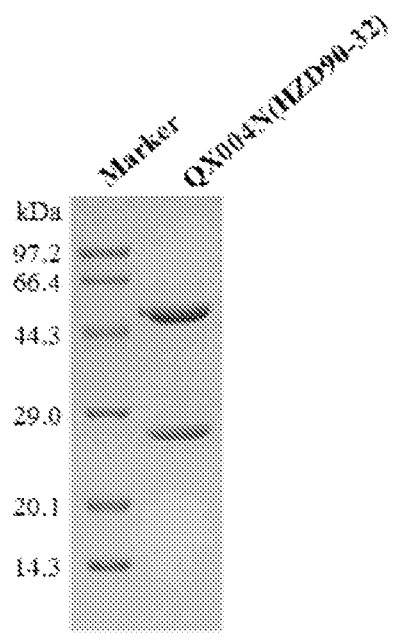
FIG. 3 shows the electrophoretic detection results of QX004N (HZD90-32).

The culture supernatant was harvested 4-8 days after transfection, and was further purified with ProteinA in one step. The purified antibody was detected by SDS-PAGE electrophoresis, and named as QX004N (HZD90-32). The result of the detection of detecting the antibody by protein electrophoresis is shown in FIG. 3. The protein electrophoresis was detected using denatured reducing gel. The result in FIG. 3 shows that there are two bands, and the sizes of the two bands are about 50 kDa and 25 kDa respectively, which are consistent with the theoretical molecular weights of the heavy chain (49.1 kDa) and light chain (23.1 kDa).

Example 2: Detection of Equilibrium Dissociation Constant ($K_D$)

The affinity of QX004N (HZD90-32) binding to IL-23 was detected using BiacoreT200, and all processes were carried out at 25° C. Commercialized Protein A chip was used to immobilize an appropriate amount of antibody by capture method, the Rmax was about 50 RU and the capture flow rate was 10 μl/min. The antigen was diluted by gradient, and the flow rate of the instrument was switched to 30 μl/min. The diluted antigen flowed through the reference channel and the channel of immobilized antibody in sequence from low to high concentration, and flowed through the buffer as negative control. The chip was regenerated with glycine at pH 1.5 after each binding and dissociation. Fitting was performed with the 1:1 binding model in the Kinetics option using the build-in software in the instrument, and the association rate constant $k_a$, dissociation rate constant ka and equilibrium dissociation constant $K_D$ of the antibody were calculated.

In addition, the affinity of QX004N (HZD90-32) was compared with the currently commercialized monoclonal antibodies against IL-23, i.e., Guselkumab and Risankizumab. The detection method for known antibodies was the same as the detection method for QX004N. The results are shown in Table 1, wherein, Guselkumab and Risankizumab were obtained by purchasing commercially available drugs.

TABLE 1

| Affinity of antibodies binding to human IL-23 | | | |
|---|---|---|---|
| Sample name | $k_a$ ($10^5$ $M^{-1}S^{-1}$) | $k_a$ ($10^{-5}$ $S^{-1}$) | $K_D$ ($10^{-10}$M) |
| Guselkumab | 5.01 | 3.19 | 0.63 |
| Risankizumab | 7.06 | 3.70 | 0.52 |
| QX004N(HZD90-32) | 3.66 | 3.50 | 1.01 |

The data in the table were: obtained by calculating the average value of the test results after each sample was tested twice.

Example 3: Activities of QX004N, Guselkumab and Risankizumab Inhibiting Phosphorylation of STAT3 in HEK Blue™ IL-23 Cells Induced by IL-23

The activities of QX004N, Guselkumab and Risankizumab inhibiting phosphorylation of intracellular signal molecule STAT3 induced by IL-23 were detected using HEK Blue™ IL-23 cell reporter gene cell line: cells in culture media were added into 96-well plate at 4×10+ cells per well, and cultured overnight in $CO_2$ incubator (37° C., 5% $CO_2$). IL-23 was diluted to Ing/ml, the antibody was diluted to a series of dilutions with a concentration range of 0 to 2 μg/ml, and IL-23 was mixed with the gradient diluted antibody in equal volumes, incubated in $CO_2$ incubator (37° C., 5% $CO_2$) for 1.5 hours, then the mixed solutions were added to the cells and cultured in $CO_2$ incubator (37° C., 5% $CO_2$) for 24 hours. The cell culture supernatant was collected and added with 10% QUANTI-Blue™ detection reagent to react at 37° C. for 1 hour, then the OD value at 630 nm was detected and the dose effect curve was plotted to analyze the neutralization activity of the antibody. The dose effect curve is shown in FIG. 4.

Figure 4:
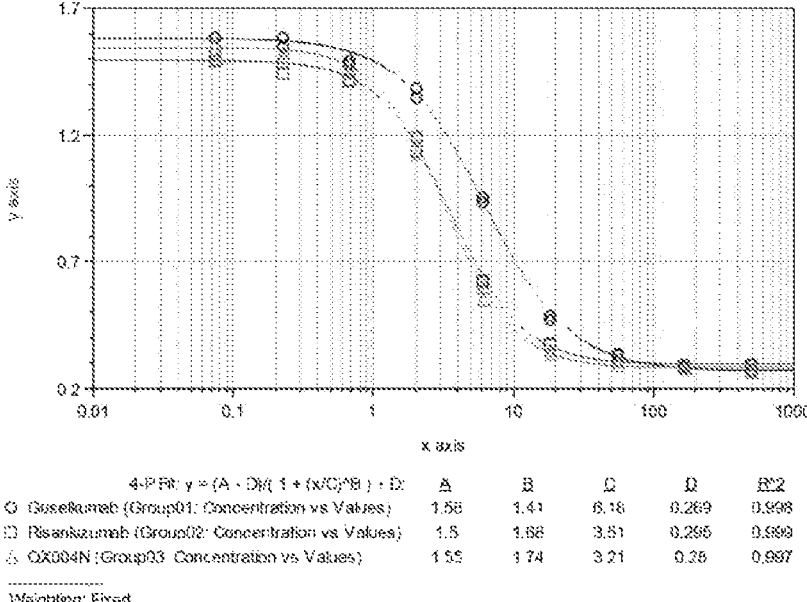
FIG. 4 shows the activities of QX004N (HZD90-32), Guselkumab and Risankizumab inhibiting the phosphorylation of STAT3 in HEK Blue™ IL-23 cells induced by IL-23.

FIG. 4 shows that QX004N can inhibit phosphorylation activity of STAT3 in HEK Blue™ IL-23 cells induced by IL-23, with an $IC_{50}$ value of 3.21 ng/ml; Guselkumab and Risankizumab can also inhibit phosphorylation activity of STAT3 in HEK Blue™ IL-23 cells induced by IL-23, with $IC_{50}$ values of 6.18 ng/ml and 3.51 ng/ml, respectively, indicating that the activity of QX004N inhibiting signal transduction induced by IL-23 is comparable to that of the commercialized monoclonal antibody against IL-23 (i.e., Risankizumab), and is superior to that of Guselkumab.

Example 4: Activities of QX004N, Guselkumab and Risankizumab Inhibiting Release of IL-17A from Mouse Spleen Cells Induced by IL-23

The activities of QX004N, Guselkumab and Risankizumab inhibiting release of IL-17A induced by IL-23 were tested using mouse spleen cells: primary mouse spleen cells were obtained from mouse spleen, and cells in the culture media were added into 96-well plate at $5 \times 10^5$ cells per well. IL-23 was diluted to 10 ng/ml, the antibody was diluted to a series of dilutions with a concentration range of 0 to 20 μg/ml, and IL-23 was mixed with the gradient diluted antibody in equal volumes, incubated in $CO_2$ incubator (37° C., 5% $CO_2$) for 1.5 hours, then the mixed solution was added to the cells and cultured in $CO_2$ incubator (37° C., 5% $CO_2$) for 48 hours. The cell culture supernatant was collected to detect the expression amount of IL-17A with ELISA Kit and the dose effect curve was plotted to analyze the neutralization activity of the antibody. The dose effect curve is shown in FIG. 5.

Figure 5:
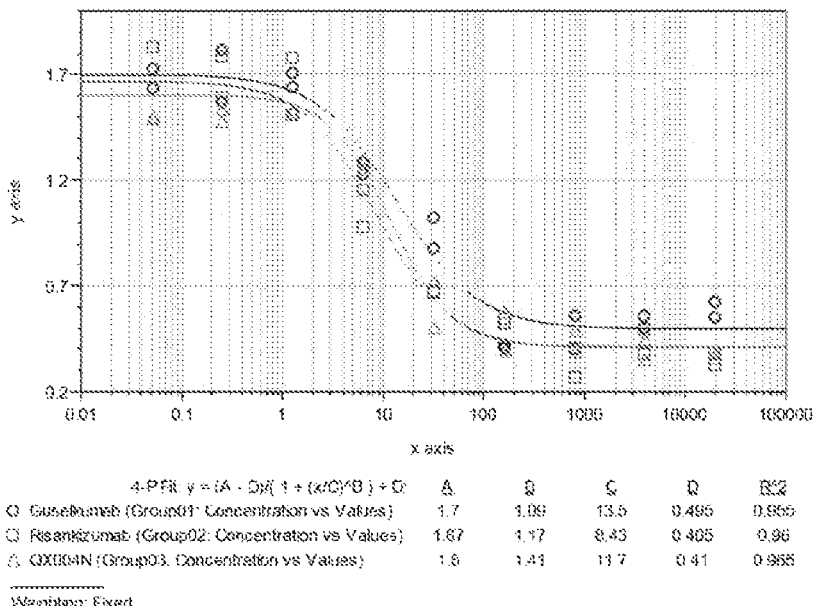
FIG. 5 shows the activities of QX004N (HZD90-32), Guselkumab and Risankizumab inhibiting the release of IL-17A from mouse spleen cells induced by IL-23.

FIG. 5 shows that QX004N can inhibit the activity of the release of IL-17A from mouse spleen cells induced by IL-23, with an $IC_{50}$ value of 11.7 ng/ml; Guselkumab and Risankizumab can also inhibit the activity of the release of IL-17A from mouse spleen cells induced by IL-23, with $IC_{50}$ values of 13.5 ng/ml and 8.43 ng/ml, respectively, indicating that the activity of QX004N inhibiting release of IL-17A from mouse spleen cells induced by IL-23 is strong, which is comparable to the existing commercialized products (Guselkumab and Risankizumab).

Example 5: Activities of QX004N, Guselkumab and Risankizumab Inhibiting Release of IFN-γ from Human NK Cells Induced by IL-23

The activities of QX004N, Guselkumab and Risankizumab inhibiting release of IFN-γ induced by IL-23 were detected using human NK cells: peripheral blood mononuclear cells (PBMCs) were isolated from the peripheral blood of healthy volunteers by density gradient centrifugation, and natural killer cells (NK cells) were separated from PBMCs by magnetic bead sorting. 100 U/ml of IL-2 was added into $CO_2$ incubator (37° C., 5% $CO_2$) for activation and culture for 3 days. 20 ng/ml of IL-18 was added into the culture media, then the cells in the culture media were added into 96-well plate at $1\times10^5$ cells per well. IL-23 was diluted to 10 ng/ml, the antibody was diluted to a series of dilutions with a concentration range of 0 to 5 μg/ml, and IL-23 was mixed with the gradient diluted antibody in equal volume, incubated in $CO_2$ incubator (37° C., 5% $CO_2$) for 1.5 hours, then the mixed solution was added to the cells and cultured in $CO_2$ incubator (37° C., 5% $CO_2$) for 48 hours. The cell culture supernatant was collected to detect the expression amount of IFN-γ with ELISA Kit and the dose effect curve was plotted to analyze the neutralizing activity of the antibody. The dose effect curve is shown in FIG. 6.

Figure 6:
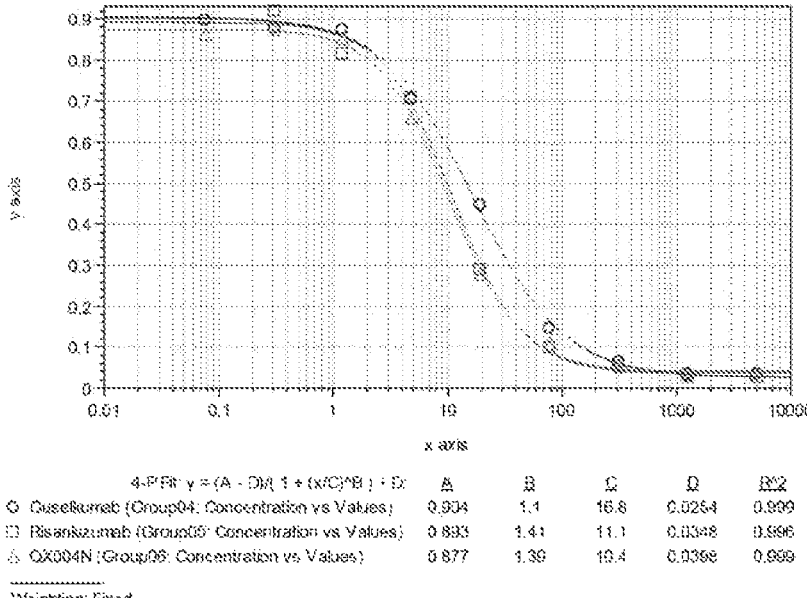
FIG. 6 shows the activities of QX004N (HZD90-32), Guselkumab and Risankizumab inhibiting the release of IFN-γ from human NK cells induced by IL-23.

FIG. 6 shows that QX004N can inhibit the activity of release of IFN-γ from human NK cells induced by IL-23, with an $IC_{50}$ value of 10.4 ng/ml; Guselkumab and Risankizumab can also inhibit the activity of the release of IFN-γ from human NK cells induced by IL-23, with $IC_{50}$ values of 16.8 ng/ml and 11.1 ng/ml, respectively, indicating that the activity of QX004N inhibiting the release of IFN-γ from human NK cells induced by IL-23 is stronger than that of the currently commercialized product, Guselkumab, and is comparable to that of Risankizumab.

It can be seen from above Examples 3 to 5 that, QX004N is superior to Guselkumab and comparable to Risankizumab in three measured biological activities at the cellular level. Whereas it has been proved in clinical trials that Risankizumab (SKYRIZIR) has significant therapeutic effect on moderate to severe plaque psoriasis, QX004N is also expected to show good clinical effect in the prevention and treatment of related diseases.

Example 6: Detection of the Binding Specificity of QX004N, Guselkumab and Risankizumab to the p19 Subunit of IL-23

The binding of QX004N, Guselkumab and Risankizumab to the p40 subunit of IL-23 was detected by Binding ELISA. IL-23-p40 was diluted to 2 μg/ml, added to the ELISA plate, and coated overnight at 4° C. After blocking, a series of antibody dilutions diluted to a concentration ranging from 0 to 5 μg/ml and Goat-anti-human IgG secondary antibody were added respectively for incubation, finally substrate was added for color development, and the termination solution was added to terminate the color reaction. After termination, the ELISA plate was placed in a microplate reader to read the absorption value at 450 nm (the absorption value at 650 nm was taken as reference), and the dose effect curve was plotted to analyze the binding specificity of the antibody. The dose effect curves are shown in FIG. 7.

Figure 7:
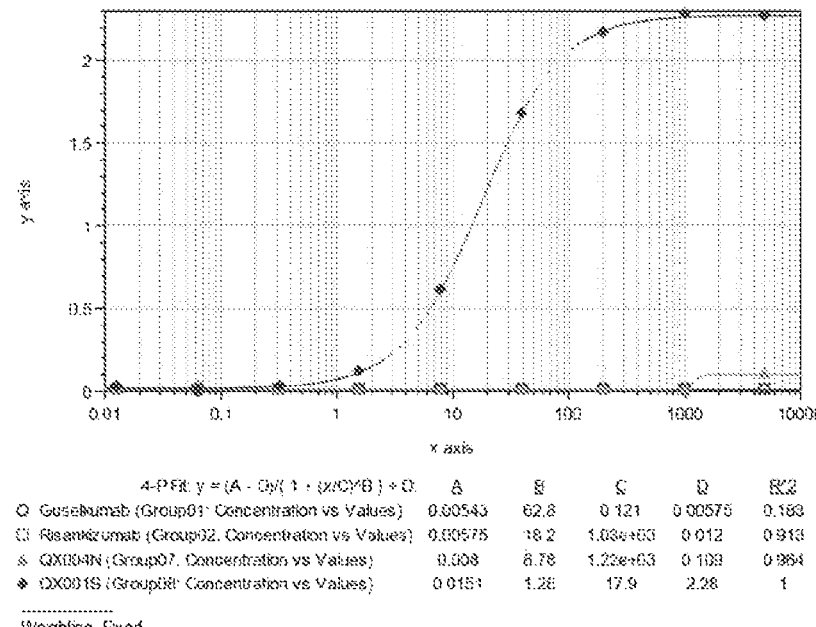
FIG. 7 shows the detection results of the binding specificity of QX004N (HZD90-32), Guselkumab and Risankizumab to the p19 subunit of IL-23.

FIG. 7 shows that the IL-23 p40 specific antibody QX001S can bind to the p40 subunit, and QX004N, Guselkumab and Risankizumab do not bind to the p40 subunit of IL-23, indicating that QX004N, Guselkumab and Risankizumab specifically bind to the p19 subunit of IL-23.

Example 7: Point Mutation was Used to Study the Difference Between QX004N and Risankizumab in Binding to IL-23p19

Mutation primers were designed through PCR method. Five p19 plasmids comprising single point mutation were constructed respectively, as shown in Table 2. The p19 mutant plasmid was co-transfected with p40 plasmid into 293F cells to prepare a cell supernatant containing the IL-23 mutant. The protein concentration of IL-23 mutants in the cell supernatants was quantified by quantitative ELISA, and then the $EC_{50}$ values of QX004N, Risankizumab and different IL-23 mutants were detected by Binding ELISA.

Concentration of the cell supernatant comprising IL-23 mutant was quantified by Binding ELISA: anti-p40 antibody was diluted to 2 μg/ml and added to the ELISA plate, and coated overnight at 4° C. After blocking, purified IL-23 diluted to a known concentration ranging from 0 to 50 ng/ml and the gradient diluted cell supernatant comprising IL-23 mutant was added for incubation. Then Biotin labeled anti-His antibody and SA-HRP were added respectively to incubation, finally the substrate was added for color development, and the termination solution was added to terminate the color reaction. After termination, the ELISA plate was placed in a microplate reader to read the absorption value at 450 nm (the absorption value at 650 nm was taken as reference), and the dose effect curve of purified IL-23 with known concentration was plotted as the standard curve, and then the concentration of cell supernatant of IL-23 mutant was calculated according to the standard curve and the OD value of cell supernatant of IL-23 mutant.

The binding of QX004N and Risankizumab to IL-23 mutant was detected by Binding ELISA: QX004N and Risankizumab were respectively diluted to 1 μg/ml and added to the ELISA plate, and coated overnight at 4° C. After blocking, a series of cell supernatant dilutions of IL-23 mutant diluted to a concentration ranging from 0 to 0.5 μg/ml for incubation. Then, Biotin labeled anti-His antibody and SA-HRP were added respectively for incubation, finally the substrate was added for color development, and the termination solution was added to terminate the color reaction. After termination, the ELISA plate was placed in a microplate reader to read the absorption value at 450 nm (the absorption values at 650 nm was taken as reference), and the dose effect curve was plotted and the $EC_{50}$ value was calculated. If the $EC_{50}$ value of the IL-23 mutant is more than 10 times higher than that of the natural IL-23, it indicates that the site corresponding to the mutation is an antibody binding epitope. The $EC_{50}$ results are shown in Table 2.

The result in Table 2 shows that the epitopes for QX004N and Risankizumab binding to IL-23 p19 are different, and W137 is the key epitope for QX004N. Jutta Schröder and Yehudi Bloch et al. respectively confirmed that W137 is one of the key sites for IL-23p19 binding to IL-23 receptor (IL-23R).

TABLE 2

| Binding of antibodies to different IL-23 mutants detected by BindingELISA | | |
|---|---|---|
| | $EC_{50}$(ng/ml) | |
| IL-23 mutants | QX004N | Risankizumab |
| Natural IL-23 | 1.7 | 1.8 |
| W137A | 50.1 | 2.3 |
| W137D | 363.0 | 5.2 |
| L140P | N.D. | 54.4 |
| R143A | 3.4 | 307.0 |
| F144S | N.D. | 10.1 |

N.D: indicating the binding is weak, and the $EC_{50}$ value is not accurate.

In conclusion, the monoclonal antibody of the present application can inhibit the STAT3 phosphorylation activity, IL-17A release activity of mouse spleen cells induced by IL-23, and IFN-γ release activity of human NK cells induced by IL-23. Its inhibitory activity is superior to that of the currently commercialized product (i.e., Guselkumab), and is comparable to that of Risankizumab. For IL-17A release activity of mouse spleen cells induced by IL-23, the activity of the monoclonal antibody of the present application inhibiting the release of IL-17A from the mouse spleen cells induced by IL-23 is comparable to that of Guselkumab and Risankizumab.

Like the currently commercialized products (Guselkumab and Risankizumab), the monoclonal antibody of the present application can specifically bind to the p19 subunit of IL-23. However, the monoclonal antibody of the present application is different from Guselkumab and Risankizumab in binding epitopes of IL-23p19. W137 is the key epitope for the monoclonal antibody of the present application, but not the key epitope for Guselkumab or Risankizumab (the epitope research of Guselkumab can be found in the international patent publication WO2007076524A2; the epitope research of Risankizumab can be found in "Sanjaya et al., Selective targeting of the IL23 pathway Generation and characterization of a new high affinity humanized anti IL23A antibody, mAbs, Volume 7, Issue 4, 2015").

In addition, due to Risankizumab (SKYRIZI®) has been approved for marketing in Japan, the United States and the European Union, and the clinical trial results show that its therapeutic effect on moderate to severe plaque psoriasis is superior to that of Johnson & Johnson's blockbuster anti-inflammatory drug STELARA® (ustekinumab) and AbbVie's best-selling anti-inflammatory drug HUMIRA® (adalimumab), the monoclonal antibody of the present application is expected to show good clinical effects in the prevention and treatment of related diseases.

The invention claimed is:

1. An isolated anti-human interleukin 23 monoclonal antibody, comprising three heavy chain complementary determining regions (CDR-H1, CDR-H2 and CDR-H3) and three light chain complementary determining regions (CDR-L1, CDR-L2 and CDR-L3), wherein:

(a) the amino acid sequence of CDR-H1 consists of SEQ ID NO: 1;

(b) the amino acid sequence of CDR-H2 consists of SEQ ID NO: 2;

(c) the amino acid sequence of CDR-H3 consists of SEQ ID NO: 3;

(d) the amino acid sequence of CDR-L1 consists of SEQ ID NO: 4;

(e) the amino acid sequence of CDR-L2 consists of SEQ ID NO: 5; and (f) the amino acid sequence of CDR-L3 consists of SEQ ID NO: 6.

2. The monoclonal antibody according to claim 1, which comprises a heavy chain variable region and a light chain variable region, wherein the amino acid sequence of the heavy chain variable region consists of SEQ ID NO: 7; and, the amino acid sequence of the light chain variable region consists of SEQ ID NO: 8.

3. A pharmaceutical composition, comprising the monoclonal antibody according to claim 1, and a pharmaceutically acceptable carrier.

4. The pharmaceutical composition according to claim 3, which is used for treatment of a disease related to IL-23 mediated signal transduction;

wherein the disease related to IL-23 mediated signal transduction is selected from the group consisting of: psoriatic arthritis, inflammatory bowel disease, and psoriasis.

5. The pharmaceutical composition according to claim 4, wherein the inflammatory bowel disease is ulcerative colitis or Crohn's disease.

* * * * *